(12) United States Patent
Krishnamurthy et al.

(10) Patent No.: US 7,466,323 B2
(45) Date of Patent: Dec. 16, 2008

(54) KEY IMAGE NOTE DISPLAY AND ANNOTATION SYSTEM AND METHOD

(75) Inventors: Anand Krishnamurthy, Bangalore (IN); Muthu Venkatesh Muthuraj, Kenosha, WI (US); Benjamin D. Novatzky, Oak Park, IL (US); Steven Lawrence Fors, Chicago, IL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 146 days.

(21) Appl. No.: 10/453,559

(22) Filed: Jun. 3, 2003

(65) Prior Publication Data

US 2004/0246270 A1   Dec. 9, 2004

(51) Int. Cl.
G09G 5/377 (2006.01)
G06T 11/60 (2006.01)

(52) U.S. Cl. ..................... 345/634
(58) Field of Classification Search ............. 345/634, 345/636, 637
See application file for complete search history.

(56) References Cited

U.S. PATENT DOCUMENTS 6,240,308 B1 * 5/2001 Hardy et al. .............. 345/634
6,429,878 B1 * 8/2002 Turek et al. ............... 345/636
2002/0016718 A1 * 2/2002 Rothschild et al. ........... 705/2
2002/0171669 A1 * 11/2002 Meron et al. .............. 345/619
2004/0205542 A1 * 10/2004 Bargeron et al. ........... 715/512
2004/0249850 A1 * 12/2004 Kuth ....................... 707/102
2006/0061595 A1 * 3/2006 Goede et al. .............. 345/619

FOREIGN PATENT DOCUMENTS

WO   WO 03036513 A2 * 5/2003

* cited by examiner

*Primary Examiner*—Jeffery A. Brier
(74) *Attorney, Agent, or Firm*—Fletcher Yoder

(57) ABSTRACT

A method and apparatus for displaying annotations on a digital image such that the viewing area is simplified and maximized. Abbreviated reason codes are employed, thereby increasing the number of annotations that may be displayed concurrently with an image and reducing the obtrusiveness of the annotations. The abbreviated reason codes may provide information to viewers about the significance of the image. Viewers may configure where the annotations are displayed and may associate priorities with the reason codes such that annotations of interest may be displayed more prominently or accessibly. Likewise, text descriptions associated with an annotation may be hidden until requested by a viewer. In instances where the number of annotations exceeds some configurable threshold, the excess annotations may be hidden unless requested.

24 Claims, 3 Drawing Sheets

KEY IMAGE NOTE DISPLAY AND ANNOTATION SYSTEM AND METHOD

BACKGROUND OF THE INVENTION

The present technique relates generally to the presentation of digital images and more particularly to the use of operator selected or provided notations with an image data set. More specifically, the present technique relates to the use of key image notes with digital medical images.

Various technical fields engage in some form of image processing in which the evaluation, analysis and subsequent presentation of image data is a primary goal. In performing these functions, trained personnel may desire to notate one or more images in a data set for it's significance or insignificance to certain subsequent viewers. For example, medical imaging technologies produce various types of diagnostic images which radiologist may preliminarily evaluate for quality and for interest or significance to others, such as surgeons, referring or reviewing physicians, teachers, therapists, researchers, or the patient.

For example, in the field of medical imaging, key image notes (KIN's) provide a mechanism for indicating the significance of an image to a particular viewer or group of viewers. Each KIN comprises various attributes including a reason code signifying the basis for the note, an optional text description provided by the user, and a reference to the image or images to which the KIN refers. In large image data sets or for images which may be of interest to a variety of viewers, it may be difficult to provide the desired images and KIN's to specific viewers using a simple interface. In particular, despite the overall desire for a simple interface, it is not uncommon for several KIN's to reference the same image, thereby complicating the interface. In addition, multiple images may be displayed simultaneously, leaving little room for the display of the KIN's associated with each image. For example, the display of the various KIN's as text annotations on a displayed image or images may lead to a cluttered or obscured image. Similarly, the use of icons or other representations to signify the presence of KIN's associated with an image may introduce additional steps if the operator is required to interact with the icon to access the KIN's and any additional information.

Similarly, in other fields, other forms of evaluation and notation for subsequent viewing may occur. For example, non-invasive imaging of package and baggage contents may annotated or prioritized for subsequent review. In addition, the analysis of satellite and radar weather data may involve evaluation and annotation of weather formations, such as rotations and pressure fronts, present in the image data. Likewise, evaluation of astronomical and geological data represented visually may also involve similar evaluation and annotation exercises.

With the development of digital imaging and image processing techniques, the quantity of readily available image data requiring evaluation and analysis in many of these technical fields has increased substantially. Likewise, the ability to provide multiple annotations of varying priority to a particular viewer is greatly increased in digital imaging and processing. There is a need, therefore, for techniques for evaluating and notating large numbers of digital images for a variety of subsequent viewers in a concise and straightforward manner such that the images and information of greatest interest to a viewer are readily accessible.

BRIEF DESCRIPTION OF THE INVENTION

The present technique is directed to the display of annotations on a digital image in a space maximizing and simplified manner. In particular, the technique is directed to providing truncated or abbreviated reason codes such that multiple annotations may be associated with one or more images in an unobtrusive manner. The truncated reason codes allow space to be maximized on the image while still providing information to subsequent viewers about the significance of the image. Viewers may configure where the truncated reason codes are displayed and may associate priorities with the reason codes such that reason codes of interest are displayed more prominently or accessibly. Likewise, descriptions associated with an annotation may be hidden until requested by a viewer. In instances where the number of annotations exceeds some configurable threshold, the annotations in excess of the threshold may be hidden from view.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

The present technique pertains to the evaluation and notation of digital image data of various sorts, including analog image data that has been digitized. For simplicity, and in accordance with a presently contemplated implementation, the following example discusses the technique in the context of medical imaging. However it is to be understood that the technique is not limited to medical imaging. Instead, the evaluation and notation of any digital images or sets of images may benefit from the following technique. Digital image data of a general or technical nature, such as security, meteorological, astronomical, geological and medical, which may employ viewer specific notations or multiple notations per image may benefit from the present technique.

Figure 1:
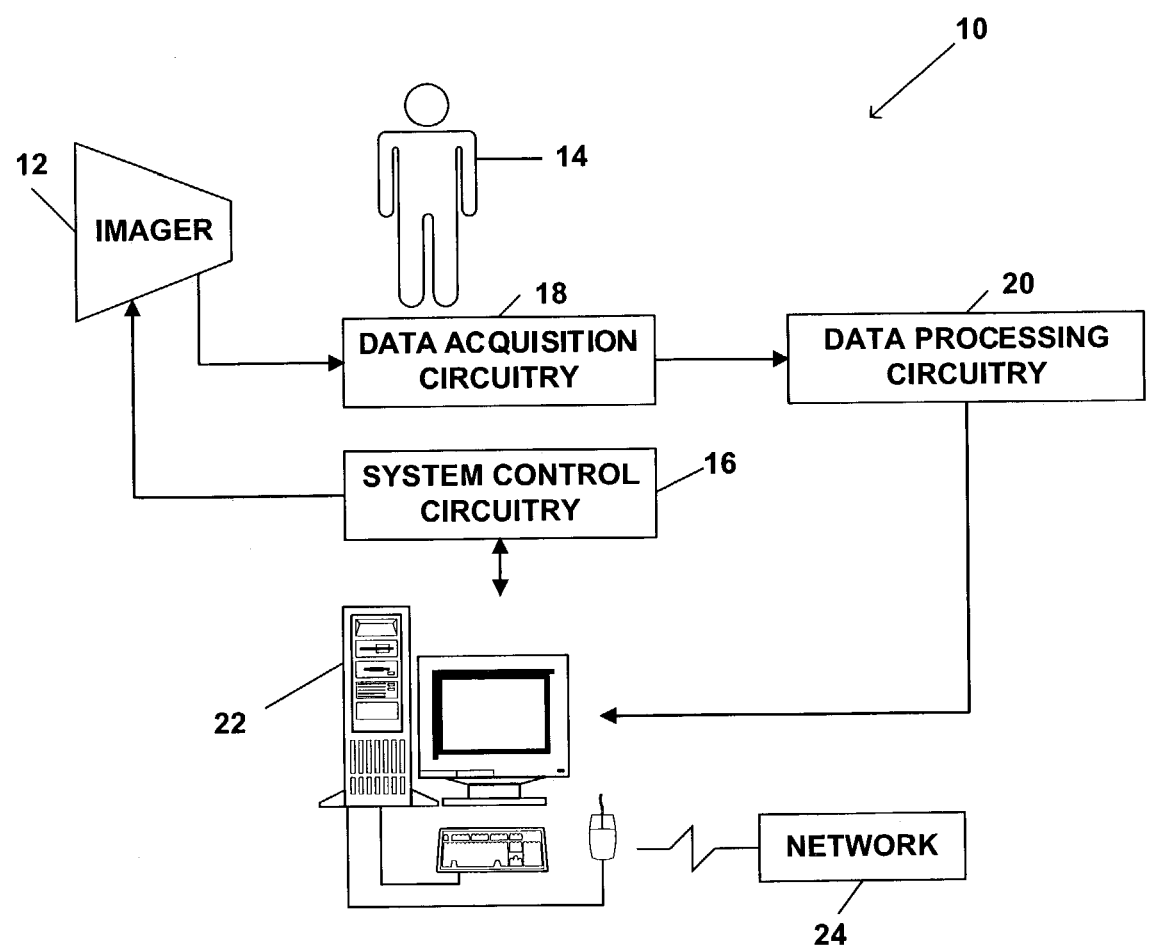
FIG. 1 is a general diagrammatical representation of certain functional components of an exemplary image data-producing system, in the form of a medical diagnostic imaging system.

In the context of medical imaging, various imaging resources may be available for diagnosing medical events and conditions in both soft and hard tissue, and for analyzing features and function of specific anatomies. FIG. 1 provides a general overview for exemplary imaging systems, and subsequent figures offer somewhat greater detail into the major system components of a specific modality system. Such medical imaging systems may include, but are not limited to, medical imaging modalities such as digital X-ray, Computed Tomography (CT), computed radiography, Magnetic Resonance Imaging (MRI), Positron Emission Tomography (PET), thermoacoustic imaging, film-based optical imaging, ultrasound imaging, and nuclear medicine-based imaging.

Referring to FIG. 1, an imaging system 10 generally includes some type of imager 12 which detects signals and converts the signals to useful data. As described more fully below, the imager 12 may operate in accordance with various physical principles for creating the image data. In general, however, in the medical imaging context image data indicative of regions of interest in a patient 14 are created by the imager in a digital medium.

The imager 12 operates under the control of system control circuitry 16. The system control circuitry may include a wide range of circuits, such as radiation source control circuits, timing circuits, circuits for coordinating data acquisition in conjunction with patient or table of movements, circuits for controlling the position of radiation or other sources and of detectors, and so forth. The imager 12, following acquisition of the image data or signals, may process the signals, such as for conversion to digital values, and forwards the image data to data acquisition circuitry 18. In digital systems, the data acquisition circuitry 18 may perform a wide range of initial processing functions, such as adjustment of digital dynamic ranges, smoothing or sharpening of data, as well as compiling of data streams and files, where desired. The data are then transferred to data processing circuitry 20 where additional processing and analysis are performed. For the various digital imaging systems available, the data processing circuitry 20 may perform substantial analyses of data, ordering of data, sharpening, smoothing, feature recognition, and so forth.

Ultimately, the image data are forwarded to some type of operator interface 22 for viewing and analysis. While operations may be performed on the image data prior to viewing, the operator interface 22 is at some point useful for viewing reconstructed images based upon the image data collected. The images may also be stored in short or long-term storage devices, for the present purposes generally considered to be included within the interface 22, such as picture archiving communication systems. The image data can also be transferred to remote locations, such as via a network 24. It should also be noted that, from a general standpoint, the operator interface 22 affords control of the imaging system, typically through interface with the system control circuitry 16. Moreover, it should also be noted that more than a single operator interface 22 may be provided. Accordingly, an imaging scanner or station may include an interface which permits regulation of the parameters involved in the image data acquisition procedure, whereas a different operator interface may be provided for manipulating, enhancing, and viewing resulting reconstructed images.

Figure 2:
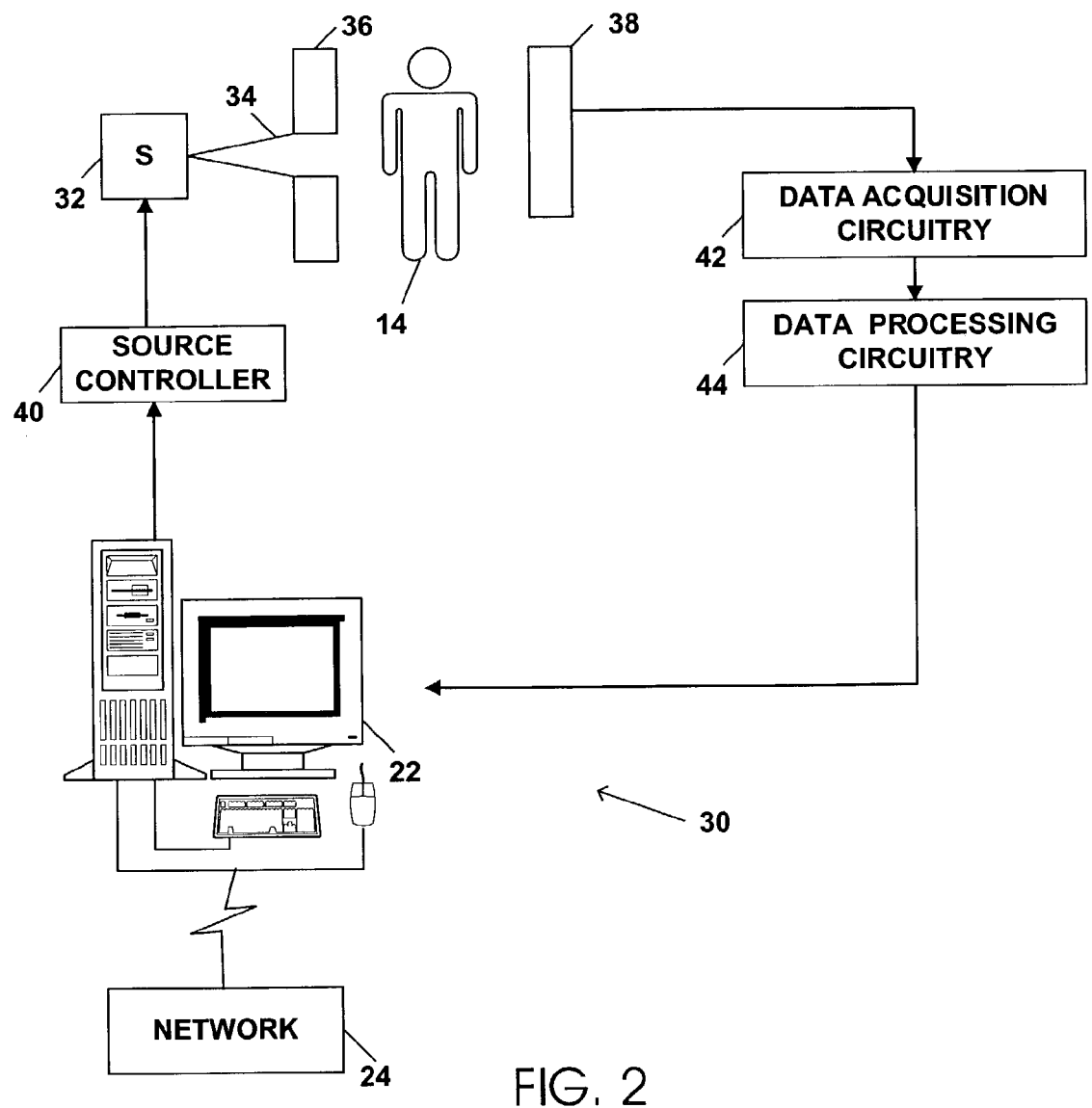
FIG. 2 is a diagrammatical representation of a particular imaging system of the type shown in FIG. 1, in this case an exemplary X-ray imaging system which may be employed in accordance with certain aspects of the present technique.

To discuss the technique in greater detail, a specific medical imaging modality based upon the overall system architecture outlined in FIG. 1 is depicted in FIG. 2. FIG. 2 generally represents a digital X-ray system 30. System 30 includes a radiation source 32, typically an X-ray tube, designed to emit a beam 34 of radiation. The radiation may be conditioned or adjusted, typically by adjustment of parameters of the source 32, such as the type of target, the input power level, and the filter type. The resulting radiation beam 34 is typically directed through a collimator 36 which determines the extent and shape of the beam directed toward patient 14. A portion of the patient 14 is placed in the path of beam 34, and the beam impacts a digital detector 38.

Detector 38, which typically includes a matrix of pixels, encodes intensities of radiation impacting various locations in the matrix. A scintillator converts the high energy X-ray radiation to lower energy photons which are detected by photodiodes within the detector. The X-ray radiation is attenuated by tissues within the patient, such that the pixels identify various levels of attenuation resulting in various intensity levels which will form the basis for an ultimate reconstructed image.

Control circuitry and data acquisition circuitry are provided for regulating the image acquisition process and for detecting and processing the resulting signals. In particular, in the illustration of FIG. 2, a source controller 40 is provided for regulating operation of the radiation source 32. Other control circuitry may be provided for controllable aspects of the system, such as a table position, radiation source position, and so forth. Data acquisition circuitry 42 is coupled to the detector 38 and permits readout of the charge on the photo detectors following an exposure. In general, charge on the photo detectors is depleted by the impacting radiation, and the photo detectors are recharged sequentially to measure the depletion. The readout circuitry may include circuitry for systematically reading rows and columns of the photo detectors corresponding to the pixel locations of the image matrix. The resulting signals are then digitized by the data acquisition circuitry 42 and forwarded to data processing circuitry 44.

The data processing circuitry 44 may perform a range of operations, including adjustment for offsets, gains, and the like in the digital data, as well as various imaging enhancement functions. The resulting data are then forwarded to an operator interface or storage device for short or long-term storage. The images reconstructed based upon the data may be displayed on the operator interface, or may be forwarded to other locations, such as via a network 24, for viewing. Also, digital data may be used as the basis for exposure and printing of reconstructed images on a conventional hard copy medium such as photographic film.

When in use, the digital X-ray system 30 acquires digital X-ray images of a portion of the patient 14 which may then be analyzed for the presence of indicia of one or more medical pathologies such as nodules, lesions, fractures, microcalcifications, etc. Other imaging modalities of course may be better suited for detecting different types of anatomical features.

In practice, a clinician may evaluate one or more medical image, such as an X-ray, and may assess of image quality as well as detect features or features of diagnostic significance within the image. Based upon her observations, the clinician may associate a key image note (KIN) with an image deemed significant. Indeed, the clinician may associate more than one KIN with an image or may associate the same KIN with multiple images.

A KIN is an object conforming to the Digital Image and Communications in Medicine (DICOM) standard and possesses various attributes. For example, unlike simple text annotations, a KIN may be associated with multiple images, may be the basis for queries, and may be exported. The KIN generally comprises a reference to the image or images with which the KIN is associated and a reason or reason code indicating the significance of the associated images. The reasons may be selected from a set of predetermined reasons, such as those specified in the DICOM standard. Examples of such predetermined reasons include "Rejected for Quality Reasons," "For Referring Provider," "For Peer Review," and so forth. In addition, the KIN may include textual descriptions or comments input by a viewer or CAD routine or other optional fields.

Because of the potential association of multiple KIN's with an image and the potential lengthiness of the provided reasons and text descriptions, it may be difficult to provide a simple and intuitive user interface providing the KIN data with an image. In particular, the space available to display a KIN may be very limited after allocation of space to the image and to other annotations and information associated with the image. The space situation may be further complicated if multiple KIN's are associated with an image.

To address space concerns, each KIN reason may be represented by a key acronym text (KAT), such as a three-letter code. For example, Table 1 illustrates the KIN reasons, specified by the DICOM standards, and a respective three-letter KAT associated with each reason:

| DICOM KIN CODE | KIN REASON | KAT |
| --- | --- | --- |
| 113000 | Of Interest | INT |
| 113001 | Rejected for Quality Reasons | REJ |
| 113002 | For Referring Provider | RPD |
| 113003 | For Surgery | SUR |
| 113004 | For Teaching | TEA |
| 113005 | For Conference | CON |
| 113006 | For Therapy | TRP |
| 113007 | For Patient | PAT |
| 113008 | For Peer Review | REV |
| 113009 | For research | RSH |
| 113010 | Quality Issue | QUA |

Though three-letter KAT's have been shown by example, other formats are also possible such as one-letter, two-letter, four-letter codes and so forth. The KAT should briefly convey the lengthier reason such that an experienced viewer may determine the reason associated with the KIN at a glance and allow more KIN's to be accommodated on a display using less space. To accommodate personal preferences, the KAT for each KIN reason may be configurable, allowing each user to specify a KAT which they associate with a reason, such as TCH instead of TEA for "For Teaching" or PRV instead of RPD for "For Referring Provider." Likewise, the display location of KAT's in relation to an image may be configured to accommodate viewer preferences or to otherwise optimize the display of an image with associated notations.

In addition, a user may also configure the priorities associated with the various reasons or DICOM codes. The priorities may then be used to determine the display order or location of images or the order of presentation of KIN's associated with a displayed image. For example, a surgeon may prioritize the KIN reason SUR highest and the KIN reason REJ lowest. When the surgeon logs into the system 10 or otherwise identifies herself to the system 10 to review images prior to a surgery, those images which have been assigned a KIN with a SUR KIN reason may then be displayed first while those images with only a REJ KIN reason would be displayed last, if at all.

Figure 3:
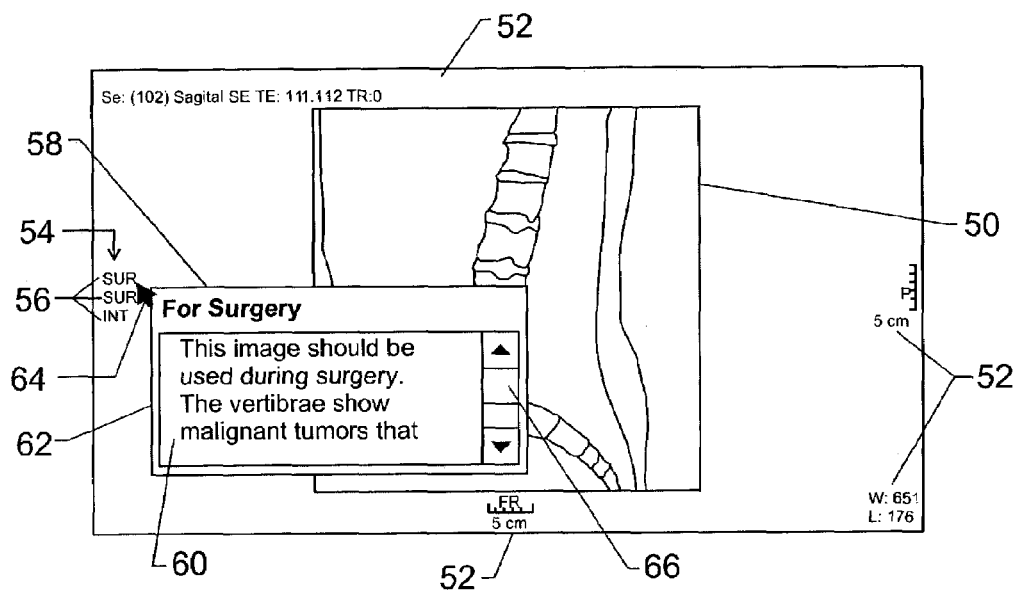
FIG. 3 is a representation of a medical image employing the present annotation techniques.

Likewise, for an image which has multiple KIN's associated with it, the viewer's assigned priorities might determine the order of listing of the KIN's. For example, referring to FIG. 3, a radiological image 50, as might appear on the display of an operator interface 22, is depicted along with various annotations 52 which provide image or patient specific information. In addition, three associated KIN's 54 are associated with the image 50, represented by the three KAT's 56 listed along the left hand side of the display. The order of display of the KAT's 56 may reflect the viewer's configured preferences. In this manner, by looking at the KIN's 54 associated with the image 50 a viewer can quickly ascertain which KIN's 54 are important, based upon the configured preferences, and thereby the significance of the image 50 in view of the preferences. In particular, by indicating a KIN 54 reason with a KAT 56 and by conveying priority information by the display order, space can be saved in the representation of multiple KIN's 54 on the same image. As depicted in FIG. 3, different KIN's 54 represented by the same KAT 56, i.e., reason code, may be associated with an image. In such cases a second configurable criteria may determine the sort order. For example, chronological order, a priority code, or the author of the KIN 54 may be used to further sort KIN's 54 having the same KAT 56.

In addition, the viewer may configure the display location of the KIN's 54 based on the KIN reason, the author, the chronology, or a priority code, or some other KIN characteristic. For example, the viewer may configure his preferences such that selected KIN's 54, such as those relating to surgery or some other procedure, are displayed at a particular location, such as the upper left corner. Similarly, the viewer may configure the display location of the KIN 54 based upon other characteristics, such as displaying all KIN's 54 authored by the viewer, a colleague, or a CAD program in a select corner and so forth. The sort order of the displayed KIN's 54 at the selected location may still be determined as discussed above.

Alternatively, the viewer may configure his preferences to filter the displayed KIN's 54. In this manner, the viewer may specify that certain KIN's 54 not be displayed based upon one or more KIN 54 characteristics. For example, a viewer may elect to not display KIN's 54 related to a certain reason codes, such as for teaching or therapy. Similarly, a viewer may elect to filter out KIN's 54 authored by a specified colleague or by a CAD program, KIN's 54 older than a specified date or age, or KIN's 54 below a specified priority code. The filtered results may then be displayed as discussed above with regard to display location or sort order.

In addition, the KIN reason 58, an associated text description 60, or both may be interactively displayed in a text box 62 in response to a user action. For example, as depicted in FIG. 3, the movement or actuation of a mouse cursor 64 over a KAT 56 may activate the display of the text box 62 which may identify the KIN reason 58 and may also display the associated text description 60. As depicted, a text description 60 which exceeds the space provide by the text box 62 may be fully accessed by means of a scroll bar 66 which may be activated using the mouse cursor 64 or via some other input mechanism. The movement of the mouse cursor 64 away from a KAT 56 may deactivate or hide the text box 62. Similarly, the movement of the mouse cursor 64 away from or out of the text box 62 may deactivate or hide the text box 62 if the mouse cursor 64 is not moved over the associated KAT 56.

In one embodiment, the displayed KIN reason 58 may be selectable by the viewer, such as via mouse cursor 64, to access a KIN 54 browser or query mechanism. The browser may provide access to additional images 50 based upon a selected KIN 54, a selected patient, a selected author, a selected date or time, and so forth.

Figure 4:
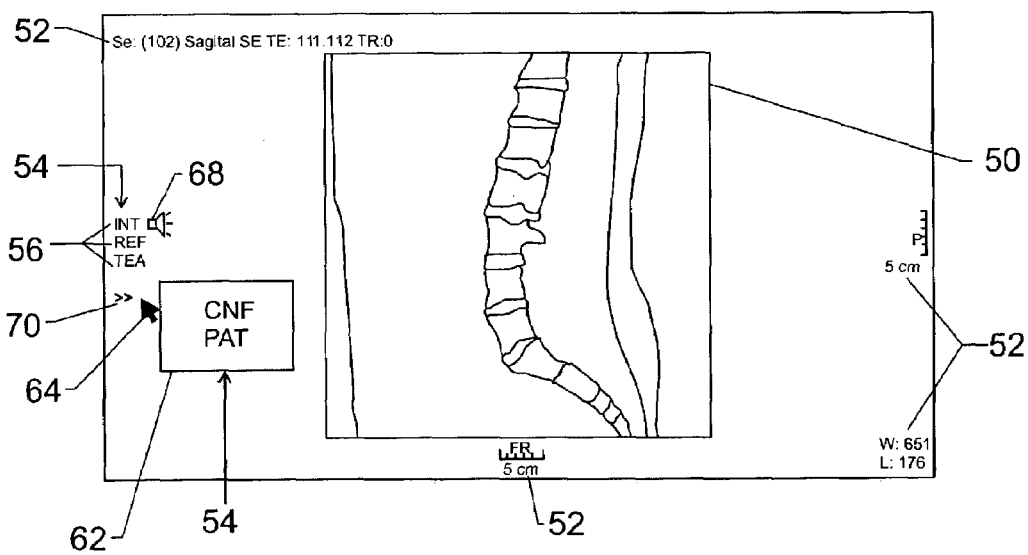
FIG. 4 is a representation of a medical image employing the present annotation techniques in which the number of notations exceed a configurable threshold.

In addition, information such as the KIN reason 58 or the associated text description 60 may be interactively provided as an audible message, such as a digital audio file, thereby allowing the image 50 to remain unobstructed. In this embodiment, the audible message may be generated by recording the comments of an operator generating the KIN 54. Alternatively, the message may be entered as text but provided audibly by a computer routine configured to translate text to speech. In these embodiments a voice indicator 68 may be displayed next to the KAT 56, as depicted in FIG. 4. The audible message may be played in response to the actions of the viewer, such as by selecting the KAT 56 with the with a mouse click or by simply passing the mouse cursor 64 over the voice indicator 68. Though an audible message may be provided for a KAT 56, a text description 60 or message may be provided as well, allowing a viewer to select the message format. The volume or other properties of an audible message may be controlled at operating system or the external speaker.

Because of the large number of KIN's 54 which may be associated with an image 50, a configurable limit may be placed upon the number of KAT's 56 displayed at one time. Referring once again to FIG. 4, if the number of KIN's 54 associated with an image 50 exceed the configurable limit, a number of KAT's 56 up to or less than the configured limit may be displayed. In one embodiment, a visual indicator 70 is displayed to indicate the presence of undisplayed KIN's 54.

In the embodiment depicted in FIG. 4, the configurable limit on displayed KIN's 54 is set to three such that the KAT's 56 for the three KIN's 54 with the highest priority, here INT, REF, and TEA, are displayed. In the depicted instance, two additional KIN's 54 are associated with the image 50. The viewer may access the additional KIN's 54 interactively. For example, in the depicted embodiment, the viewer may move the mouse cursor 64 over the visual indicator 68 to prompt the display of a text box 62 listing the KAT's 56 associated with the additional KIN's 54. The viewer may then interact with the KAT's 56 to display the associated KIN reason 58 and any available text description 60, as discussed above.

Other embodiments are, of course, possible. For example, interaction by the viewer, such as by selecting or "clicking" the visual indicator 68 via mouse cursor 64, may prompt the replacement of the displayed KIN's 54 on the display with any additional KIN's 54. Alternatively, the remaining KIN's 54 may be displayed upon interaction with a selectable menu. Similarly, the KIN's 54 associated with an image 50 may automatically displayed in groups temporally, with the highest priority KIN's 54 being displayed for a set time period, the second highest group of KIN's 54 then being displayed for a subsequent time period, and so forth. In some embodiment, therefore, a visual indicator 68 may not be present to indicate a number of KIN's 54 in excess of the configured display threshold.

If a viewer has sufficient access rights to the system 10, she may add additional KIN's 54 and associated text descriptions 60 to one or more images 50. In one embodiment, a KIN 54 added to an image 50 which already has associated KIN's 54 will be displayed according to the viewer's configured priorities and display limitations such that an added KIN 54 may or may not be displayed after addition. Similarly, the added KIN 54 may be displayed but a previously displayed KIN may no longer be displayed after the addition.

While the presently described embodiments relate to medical imaging and, in particular, to the use of key image notes with medical images, the present techniques may be applied to digital image evaluation and analysis in other contexts. For example, other contexts in which a viewer evaluates digital images and annotates the images for a variety of reasons may benefit from the disclosed techniques. Likewise, benefits may be realized in applications where it is desirable to input a textual description in association with the annotation and reason. In particular, applications in which a set of digital images are annotated for use by a variety of users having different priorities or functions may benefit from present techniques.

While the invention may be susceptible to various modifications and alternative forms, specific embodiments have been shown by way of example in the drawings and have been described in detail herein. However, it should be understood that the invention is not intended to be limited to the particular forms disclosed. In particular, though the discussed embodiments relate to medical imaging, it is to be understood than other forms of technical image analysis and non-invasive imaging, such as baggage and package screening, as well as meteorological, astronomical, geological, and non-destructive material inspection image analysis, may benefit from the discussed technique. Indeed, any form of digital image processing in which features of interest are detected and/or classified may benefit from this technique. The invention is to cover all modifications, equivalents, and alternatives falling within the spirit and scope of the invention as defined by the following appended claims.

What is claimed is:

1. A method for displaying an image, comprising:
receiving a digital image;
receiving one or more annotations associated with the digital image and, for each annotation, receiving one or more reasons why the annotation was associated with the digital image;
categorizing the one or more annotations into one or more categories of a plurality of categories based on their respective one or more reasons for association with the digital image;
receiving a priority assignment for each category of the plurality of categories; and
displaying the digital image on an operator interface, wherein the categorization of the one or more annotations associated with the digital image and the priority assignments for each category at least partially determine a display characteristic of the one or more annotations associated with the digital image.

2. The method as recited in claim 1, wherein the digital image is a medical diagnostic image.

3. The method as recited in claim 1, further comprising generating the digital image using one of a magnetic resonance imaging system, a digital X-ray system, a computed tomography imaging system, a computed radiography imaging system, a positron emission tomography system, a thermoacoustic imaging system, a film-based optical imaging system, an ultrasound imaging system, or a nuclear medicine imaging system.

4. The method as recited in claim 1, wherein the one or more annotations are provided by one or more prior reviewers and wherein the display characteristic is at least partially determined by a preference regarding the one or more annotations configured by a current reviewer.

5. The method as recited in claim 1, further comprising displaying at least one of the one or more annotations in response to a request by an operator.

6. The method as recited in claim 1, further comprising audibly providing at least one of the one or more annotations in response to a request by an operator.

7. The method as recited in claim 1, further comprising displaying one or more abbreviated codes with the digital image, wherein the one or more abbreviated codes each correspond to a respective annotation.

8. The method of claim 1, comprising:
receiving a plurality of annotations; and
receiving a plurality of digital images, wherein each of the digital images is associated with at least one annotation of the plurality of annotations;
wherein the display characteristic comprises a display order of the plurality of annotations and the digital images associated therewith.

9. The method of claim 1, wherein the display characteristic comprises a display location for the one or more annotations on the operator interface.

10. The method of claim 1, comprising displaying a KAT associated with a KIN reason of an annotation of the one or more annotations.

11. The method of claim 1, wherein the annotation comprises a KIN reason code.

12. The method of claim 1, wherein the display characteristic is a display order of the one or more annotations at least partially determined based upon a chronological order associated with the one or more annotations.

13. The method of claim 1, wherein the display characteristic is at least partially determined based upon an author associated with at least one of the one or more annotations.

14. A method for displaying a medical image, comprising:
    displaying a digital image on a display;
    filtering a set of annotations associated with the digital image to generate a set of filtered annotations, wherein the filtering is automatically performed by an electronic device based on a filtering preference received from a user, the filtering comprising analyzing each of the annotations for a characteristic undesirable to the user based on the filtering preference, and excluding any annotations having the undesirable characteristic from the set of filtered annotations; and
    displaying one or more abbreviated codes on the digital image, wherein each abbreviated code corresponds to an annotation within the set of filtered annotations.

15. The method as recited in claim 14, wherein the one or more abbreviated codes comprise abbreviations specified by a viewer preference.

16. The method as recited in claim 14, wherein the one or more abbreviated codes are displayed in a location specified by a viewer preference.

17. The method as recited in claim 14, wherein the one or more abbreviated codes are displayed in an order specified by a prioritization preference configured by the user.

18. The method as recited in claim 14, wherein the one or more abbreviated codes are displayed in accordance with a display threshold specified by a viewer preference such that the number of abbreviated codes displayed is less than or equal to the display threshold.

19. The method as recited in claim 14, comprising generating the digital image using one of a magnetic resonance imaging system, a digital X-ray system, a computed tomography imaging system, a computed radiography imaging system, a positron emission tomography system, a thermoacoustic imaging system, a film-based optical imaging system, an ultrasound imaging system, or a nuclear medicine imaging system.

20. The method as recited in claim 14, comprising displaying at least one of the one or more annotations in response to a request by an operator.

21. The method as recited in claim 14, comprising audibly providing at least one of the one or more annotations in response to a request by an operator.

22. The method as recited in claim 14, wherein filtering the set of annotations is by annotation author.

23. The method as recited in claim 14, wherein filtering the set of annotations is by category.

24. The method as recited in claim 23, wherein each categories corresponds to a KIN reason code.

* * * * *